United States Patent [19]

Iselin et al.

[11] 3,944,590
[45] Mar. 16, 1976

[54] PROCESS FOR THE TEMPORARY PROTECTION OF AMINO GROUPS IN PEPTIDE SYNTHESES

[75] Inventors: Beat Iselin, Riehen; Peter Sieber, Reinach, both of Switzerland

[73] Assignee: Ciba-Geigy Corporation, Ardsley, N.Y.

[22] Filed: Aug. 29, 1974

[21] Appl. No.: 501,565

Related U.S. Application Data

[60] Division of Ser. No. 239,721, March 30, 1972, Pat. No. 3,875,207, which is a continuation-in-part of Ser. No. 698,118, Jan. 16, 1968, abandoned.

[30] Foreign Application Priority Data
Jan. 25, 1967 Switzerland.......................... 1073/67
Aug. 28, 1967 Switzerland........................ 12038/67
Dec. 6, 1967 Switzerland........................ 17108/67

[52] U.S. Cl. .............................................. 260/463
[51] Int. Cl.² ........................................ C07C 69/96
[58] Field of Search ................................... 260/463

[56] References Cited
UNITED STATES PATENTS

| | | | |
|---|---|---|---|
| 3,467,690 | 9/1969 | Chamberlin | 260/463 |
| 3,721,714 | 3/1973 | Fenton | 260/463 X |
| 3,769,271 | 10/1973 | Southard | 260/463 X |
| 3,839,395 | 10/1974 | Otsuka et al. | 260/463 |

*Primary Examiner*—Joseph P. Brust
*Attorney, Agent, or Firm*—Joseph G. Kolodny; John J. Maitner; Theodore O. Groeger

[57] ABSTRACT

Temporary protection of amino groups by the group of the formula I

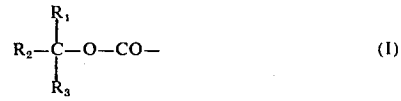

in which $R_1$ represents lower alkyl, $R_2$ lower alkyl or phenyl and $R_3$ phenyl, and wherein the phenyl radicals are unsubstituted or substituted by lower alkyl, phenyl or lower alkylphenyl groups.

7 Claims, No Drawings

PROCESS FOR THE TEMPORARY PROTECTION OF AMINO GROUPS IN PEPTIDE SYNTHESES

This is a division of application Ser. No. 239,721, filed Mar. 30, 1972 (now U.S. Pat. No. 3,875,207), which is in turn a continuation-in-part of application Ser. No. 698,118 filed Jan. 16, 1968 (now abandoned).

The present invention provides a new process for the temporary protection of amino groups in peptide syntheses by acylating the amino group and then eliminating the acyl group introduced.

As is known it is in general necessary when synthesizing peptides by coupling aminoacids or peptides to block any functional groups not participating in the coupling reaction, for example the terminal amino group or the terminal carboxyl group, the amino and carboxyl groups of the sidechains and possibly further groups such as mercapto, guanidino or hydroxyl groups. While at this stage a considerable choice of protective groups are available, they are still not quite satisfactory, especially so when long-chain and delicate peptides are to be synthesized. The problem involved is above all that in such cases hydrogenolytic elimination is out of the question (because of sulfurous aminoacids present) and the peptides are not sufficiently stable towards hydrolytically acting acid or especially alkaline agents so that the hydrolytic elimination of all protective groups in the last stage of the synthesis entails considerable losses of costly material.

It is another difficulty that the protective group located at the coupling end must be eliminated again after every coupling reaction, whereas the other protective groups should be retained until the synthesis is complete. These two types of protective groups must therefore, on one hand, be selectively eliminable with respect to each other and, on the other hand, both types must be eliminable under mild conditions.

In the peptide field, there exists therefore a need for protective groups which
  a. can be split off under mild conditions, preferably in a neutral or acid medium, so that peptide bonds of sensitive peptides are not affected;
  b. which can be split off without the use of catalysts when the peptide contains sulfurous aminoacids, for example cystine;
  c. which give good yields in each condensation method, for instance mixed anhydride method, solid phase method;
  d. which can be split off with a selectivity of about 100% from other protective groups required in the peptide synthesis;
  e. which can easily be introduced into aminoacids or peptides.

No ideal protective groups for all kinds of peptides are available. Depending on the peptide to the synthesized, it is necessary to use a different combination of protective groups.

As side-chain protective groups eliminable under mild acidic conditions the tertiary butyloxycarbonyl group (BOC) has proved particularly suitable for protecting the amino groups and the tertiary butyl ester group (tBu) for protecting the carboxyl groups, and in addition the tertiary butyl ether group is available for protecting hydroxyl groups. Apart from these groups the trityl group for example when used an an α-amino protective group, can be selectively eliminated, since in a weakly acidic medium it is much faster eliminable, for example in 80% acetic acid at room temperature 20,000 times faster. Unfortunately, however, the suitability of the trityl group as amino protective grouping is very limited. Owing to a steric hindrance it cannot be used in coupling according to the method of the activated esters and of the mixed anhydrides (except in the case of glycine) and even in the carbodiimide method it gives poor yields. Therefore, it is unsuitable for use in the synthesis of peptides starting from the carboxyl end, for example by the new method of the solid phase synthesis (cf. Merrifield, *J.AM.CHEM.SOC.* 85, 2149 [1963]). The trityl group has also other disadvantages because it is difficult to introduce and compounds protected by the trityl group are not very stable.

The present invention is based on the observation that protective groups of the formula

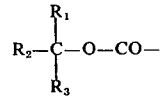

where $R_1$ is lower alkyl, $R_2$ lower alkyl or phenyl and $R_3$ represents phenyl - can be used with advantage in the synthesis of long-chain, delicate peptides, in fact with better results than known protective groups, for example the trityl group. The phenyl radicals in the above formula represent an unsubstituted phenyl ring or a phenyl ring substituted by one or two lower alkyl, phenyl or lower alkylphenyl groups. The substituents are above all in para-position, though they may also be in ortho-position or in the ortho- and parapositions. The lower alkyls contain at most 5 carbon atoms and are in the first place methyl or ethyl or, for example, propyl or butyl radicals. The lower alkyl groups are linear, though - especially in the case of the phenyl substituents - they may also be branched.

The new groups are distinguished by the fact that they are eliminable under very mild acidic conditions, for example at room temperature in about 60 to 90% aqueous acetic, chloracetic or formic acid or in a mixture of at least two of these acids and 10 to 40% of water. Since the speed at which they are eliminated is at least 600 times greater than that of the BOC group, they can be eliminated selectively with respect to this group and also to the tertiary butyl ester group, the tertiary butyl ether group and the trityl-mercapto protective group. They are therefore particularly suitable as α-amino protective groups in the synthesis of delicate peptides containing acid-labile sidechain protective groups, such as the groups just mentioned. Since they display no signs of a steric hindrance, they can be used in any desired coupling method and especially also in the solid phase synthesis.

An object of the invention is therefore a process for the temporary protection of amino groups in peptide syntheses by acylating the amino group to be protected before carrying out the coupling step(s) by a protective group of the formula I

in which $R_1$ represents lower alkyl, $R_2$ lower alkyl or phenyl, and $R_3$ stands for phenyl, and wherein the phenyl radicals are unsubstituted or substituted by lower alkyl, phenyl or lower alkylphenyl groups and splitting off the protective group after the coupling step(s) has (have) been carried out.

An object of the invention are aminoacids and peptides and derivatives thereof which are protected by a group of the formula I as defined above. A further object of the invention are means for introducing the new acyl groups.

As mentioned above, the new protective groups are especially useful for protecting aminoacids or peptides and derivatives thereof used in peptide syntheses. By peptides are to be understood in the first line those peptides which occur in nature and are, for instance, described in the text book "The Peptides" by Schroder and Lubke, Academic Press, New York and London, Volumes I and II, 1965–66, and also synthetic analogues of such peptides which differ from them by having one or more aminoacids exchanged by other aminoacids, those exchange aminoacids being known in the peptide field. By peptides are further to be understood partial sequences of the natural or synthetic peptides just mentioned. As aminoacids occurring in the peptides as building elements or structural units there may be mentioned the 20 code aminoacids, cf. for instance *Sci. American* October 1960, pg. 55, and homologues, structural isomers and optical isomers thereof, for instance amino - lower alkanoic acids with at most 7 carbon atoms other than those occurring as code aminoacids, for instance α-amino butyric acid, norvaline, norleucine, β-alanine, γ-aminobutyric acid, α,β-diaminopropionic acid, further, for instance, hydroxyproline, normethionine, phenylglycine, ornithine, citrulline, N-methyl-tyrosine and other N-lower alkyl amino-acids, further racemic and D-aminoacids.

Derivatives of peptides are especially those which have substantially the same activity as the peptides themselves, for instance C-terminal amides, especially N-unsubstituted amides, but also N-mono- or N-disubstituted amides, such as N-monoalkyl or N-dialkyl amides having up to 18, especially 1 to 5 carbon atoms in the alkyl group, or C-terminal esters, for instance alkyl esters having in the alkyl group up to 18, especially 1 to 5 carbon atoms. Other derivatives are those which are generally used as intermediates in the synthesis of peptides, for instance activated esters, hydrazides azides, mixted anhydrides and peptides or derivatives in which, besides the amino group protected according to the invention, one or more functional groups selected from amino, carboxyl, hydroxy, mercapto, and guanidino groups are protected in known manner by protective groups.

Such derivatives are also described in the above-mentioned text-book of Schröder and Lübke or in publications of Wieland et al. "Peptidsynthesen", I to V, *Angew. Chem.* 63 (1951) 7–14; l.c. 66 (1954), 507–512; l.c. 69 (1957), 362–372; l.c. 71 (1959), 417–425, l.c. 75 (1963), 539–551. Derivatives especially to be mentioned are lower alkyl esters for instance methyl ester, ethyl ester, tertiary butyl ester, tertiary amyl ester, benzyl ester, p-nitrobenzyl ester, p-methoxybenzyl ester, 2,2,2-trichloroethyl ester, 2-iodoethyl ester, p-nitrophenyl ester, 2,4-dinitrophenyl ester, 2,4,6- or 2,4,5-trichlorophenyl ester, 2,3,4,5,6-pentachlorphenyl ester, N-hydroxy- succinimide ester, and other activated esters as mentioned for instance in U.S. Pat. No. 3,035,041; further C-terminal hydrazides and azides, further mixed anhydrides, for instance anhydrides with carbonic acid lower alkyl ester such as carbonic acid methyl ester or anhydrides with lower alkanoic acids which may be halogen-substituted, for instance with formic acid, pivaloic acid, trichloracetic acid; further derivatives of aminoacids or peptides in which one or more functional groups such as amino, carboxyl, hydroxy, mercapto and/or guanidino groups are protected.

It should be noted that the protective groups of the invention can be used in any method of peptide synthesis, and that they are also especially useful in the solid phase method. They can be used in connection with any protective groups, but it is of particular advantage to use them in connection with protective groups which can be split off by means of acids, for instance the BOC group, the tert. butylester group and the tert. butyl ether group and analogous groups, because the new groups have an excellent selectivity which respect to these known groups, which are preferably used in the synthesis of sensitive peptides.

The new protective groups are introduced in known manner, similar to the BOC group, for example by way of the azide method or the method of the activated esters (for example phenyl esters, p-nitrophenyl ester, hydroxysuccinimide ester) or by reaction of carbinols of the formula $R_1R_2R_3C-OH$ with the isocyanic acid esters corresponding to the aminoacids.

The following Examples illustrate the introduction and elimination of the new group in the case of some natural α-aminoacids and of peptides synthesized from natural α-aminoacids. In the same manner the groups are used with other amino-acids and peptides.

EXAMPLE 1

Introducing the 2-phenyl-isopropyloxycarbonyl group

1. A mixture of 5.35 g (41.5 mmols) of isocyanateacetic acid ethyl ester, 4 ml of pyridine and 5.64 g (41.5 mmols) of phenyl-dimethylcarbinol is heated for 38 hours at 50°C. The yellow solution is taken up in 60 ml of ether, at 0°C agitated with molar citric acid and with water, dried over sodium sulfate and evaporated to dryness under vacuum. The residue is triturated with petroleum ether, the solid substance is filtered off and refluxed in 70 ml of hexane. The undissolved matter is filtered off, the filtrate concentrated to half its volume, filtered through 0.5 g of active carbon and the N-(2-phenyl-isopropyloxycarbonyl)-glycine ethyl ester is allowed to crystallize out; it melts at 69°–70°C. The thin-layer chromatogram of the product in chloroform reveals it to be unitary; Rf = 0.4.

A solution of 675 mg (2.55 mmols) of the ester in 10 ml of dioxane is mixed with 1.47 ml of 1.91N—NaOH and stirred for 1½ hours at room temperature. The clear solution is diluted with 20 ml of water, twice extracted with ether, and the extract is washed twice with a small quantity of water. The combined aqueous solutions are acidified at 0°C with citric acid to pH 2, twice extracted with ether, the ethereal extract is wahsed neutral, dried and filtered. Dicyclohexylamine is then added to the ethereal solution until an alkaline reaction has been established, whereupon on cratching the salt begins to crystallize out. The ethereal solution is concentrated to about 10 ml, kept for a few hours at 0°C and allowed to crystallize, then the crystals of N-(2-phenylisopropyloxycarbonyl)-glycine-dicyclohexyl ammonium salt are filtered off and washed with ether. They melt at 162° to 163°C with slight decomposition.

2. 60 Grams of phenyldimethylcarbinol (0.44 mol) in 450 ml of absolute methylenechloride and 53 ml of absolute pyridine (0.66 mol) are mixed at −5°C within 30 minutes with 67 ml of chlorocarbonic acid phenyl ester (0.53 mol) in 250 ml of absolute methylenechloride; a thick suspension forms which is stirred on for 20 hours at 0°C, then poured out over a little ice and 100 ml of methylenechloride. The resulting methylenechloride solution is repeatedly washed with water at 0°C, dried over sodium sulfate and evaporated to dryness under vacuum at 20°C. The resulting, instable mixed carbonate is immediately dissolved in 180 ml of methanol, while being cooled with ice mixed with 52 ml of hydrazinehydrate (1.06 mols) and kept at room temperature for another 20 hours. The solution is then diluted with 600 ml of ether, washed with water at 0°C, then 5 times with 0.5N-sodium hydroxide solution and with water until the washings run neutral, dried over sodium sulfate and evaporated to dryness under vacuum at 50°C. The residue (61 g) is distilled under a high vacuum, to yield 52.1 g of 2-phenyl-isopropyloxycarbonyl hydrazide in the form of a colorless, viscous oil which boils at 95°–98° under $10^{-3}$ mm Hg pressure.

20.6 Grams of the above hydrazide (0.106 mol) are dissolved in 320 ml of dimethylformamide, cooled to −20° to −30°C and mixed with 160 ml of 1.94N-hydrochloric acid, while keeping the temperature below −20°C, and then 23.2 ml of 5-molar sodium nitrite solution are dropped in at −15° to −10°C. The whole is stirred on for 15 minutes at the same temperature and then adjusted to pH = 6 to 7 with saturated potassium carbonate solution. The mixture is extracted with 800 and with 400 ml of ether, the two ethereal extracts are washed at 0°C three times with water, combined, dried over sodium sulfate and evaporated to dryness under vacuum at 30°C. The residue is cautiously distilled under a high vacuum and yields 17.5 g of the azide as a yellowish oil boiling at 47°–51°C under 0.005 mm Hg. The infrared spectrum contains the expected bands (azide band at 4.6 and 4.7$\mu$ [split up], carbonyl band at 5.8$\mu$).

2.45 G (12 mmols) of 2-phenyl-isopropyloxycarbonylazide in 14 ml of dimethylformamide are mixed with 5.75 g of N $\epsilon$ -tertiary butyloxycarbonyl-L-lysine methyl ester acetate (18 mmols) and 2 ml of dimethylformamide, and in the course of 1½ hours at 0°C 4.15 ml of triethylamine are slowly stirred in dropwise. The clear solution is kept for 3 days in a refrigerator, then diluted with 50 ml of ether and at 0°C repeatedly agitated with 0.1 molar citric acid solution and then with water until the washings run neutral, dried over sodium sulfate and evaporated to dryness. The residue is dried under a high vacuum until its weight remains constant and forms a chromatographically unitary, viscous oil. $[\alpha]_D^{20} = +6° + 0.5°$ ($c$ = 2 in chloroform). Yield: 4.83 g = 95% of the theoretical of N$^\alpha$ -(2-phenyl-isopropyloxycarbonyl)-N $^\epsilon$ -tertiary butyloxycarbonyl-L-lysine methyl ester.

In the same manner as described under (1) the paradiphenyl-isopropyloxycarbonyl group can be introduced into the glycine ethyl ester, to yield the N-(2-p-diphenyl-isopropyloxycarbonyl)-glycine ethyl ester which crystallizes from methanol and melts at 122°C.

EXAMPLE 2

Introducing the 2-p-tolyl-isopropyloxycarbonyl group

A mixture of 6.22 g (41.5 mmols) of p-tolyl-dimethylcarbinol, 4 ml of absolute pyridine and 5.35 g (41.5 mmols) of isocyanateacetic acid ethyl ester is heated for 38 hours at 50°C and then worked up as described in Example 1, to yield 9.8 g of N-(2-p-tolyl-isopropyloxycarbonyl)-glycine ethyl ester as a yellow oil; Rf = 0.25–0.35 in chloroform. For hydrolysis the ester is dissolved in 100 ml of 80% methanol and on the pH meter rapidly mixed with 24 ml of 1.9N-sodium hydroxide solution, whereupon the pH rises to 11.8. After 7 minutes, 2N-hydrochloric acid is added until pH 8.5 is reached. The resulting solution is concentrated under vacuum to about half its volume, 50 ml of water are added and the whole is extracted twice with ether. The ether solutions are washed twice with water, the combined aqueous solutions acidified at 0°C with citric acid to pH = 2 and extracted with ether. The ethereal extract is washed neutral, dried over sodium sulfate, filtered, alkalinized with dicyclohexylamine, concentrated to about 30 ml, mixed with an equal volume of petroleum ether and allowed to crystallize, to yield 8.4 g of the N-(2-p-tolylisopropyloxycarbonyl)-glycine dicyclohexyl ammonium salt melting at 145°–147° and, after recrystallization from ethyl acetate, at 147°–148°C with decomposition.

EXAMPLE 3

Eliminating the 2-phenyl-isopropyloxycarbonyl group 1. 418.6 Mg of N-(2-phenyl-isopropyloxycarbonyl)-glycine dicyclohexyl ammonium salt are dissolved at room temperature in 4.2 ml of a mixture of 7 parts by volume of glacial acetic acid, 1 part by volume of 82.8% formic acid and 2 parts by volume of water. After 4 hours thin-layer chromatographic analysis reveals that about 95% of the protecting groups have been eliminated. After standing for 6 hours at room termperature, 20 ml of acetone are added, the precipitated glycine is filtered off and thoroughly washed with acetone; it gives a clear aqueous solution and is chromatographically unitary. Yield: 68.5 mg = 91.4% of theory. Under identical conditions tertiary butyloxycarbonyl-glycine ethyl ester remains unchanged.

2. 71.7 Mg (0.27 mmol) of N-(2-phenyl-isopropyloxycarbonyl)-glycine ethyl ester are dissolved at 25°C in 1.35 ml of 80% acetic acid. After different intervals specimens of 0.2 ml each are taken, introduced into 4 ml of dimethylformamide and titrated with 0.1N-perchloric acid in glacial acetic acid (to determine the quantity of liberated glycine ethyl ester). The half-time value for the elimination of the protective group is about 2 hours. After 24 hours quantitative elimination has been achieved, and even in the thin-layer chromatogram no trace of starting material can be detected. Under identical conditions the N-protective group of N-tertiary butyloxycarbonyl-glycineethyl ester remains unchanged.

In an identical manner N-(2-p-diphenyl-isopropyloxycarbonyl)-glycine ethyl ester is split quantitatively within 3½ hours.

3. 68.8 mg of N-(2-phenyl-isopropyloxycarbonyl)-glycine ethyl ester are dissolved at room temperature in 2.6 ml of 60% chloracetic acid. After different intervals specimens of 0.20 ml each are taken, added to 4 ml of dimethylformamide and titrated with 0.1N-perchloric acid in glacial acetic acid. After 15 minutes the compound has been quantitatively split. The BOC group takes about 1900 times longer to be eliminated. In the following Table the splitting speeds for various acids and acid mixtures are listed:

| Hydrolyzing medium | Quantitative splitting after |
|---|---|
| 60% acetic acid | 12 hours |
| 90% acetic acid | 50 hours |
| 75% formic acid | immediately |
| methanol + 82.8% formic acid 1 : 1 | 11 hours |
| glacial acetic acid + 82.8% formic acid + water 7 : 1 : 2 | 4 ½ hours |
| glacial acetic acid + 82.8% formic acid + water 7 : 1 : 2 + sodium chloride | 40 minutes |

4. A solution of 439.7 mg (1.04 mmols) of $N^\alpha$-(2-phenyl-isopropyloxycarbonyl)-$N^\epsilon$-tertiary butyloxycarbonyl-L-lysine methyl ester in 4.4 ml of 80% acetic acid is kept for 48 hours at room temperature. Thin-layer chromatography after this time reveals that the $N^\alpha$-protective group has been eliminated practically quantitatively but the $N^\epsilon$-tertiary butyloxycarbonyl group has not been affected. The solution is evaporated to dryness under vacuum, and the residue is dried under a high vacuum at 45°C, then dissolved in a small quantity of ether, whereupon slow crystallization sets in; to complete this, an approximately equal quantity of petroleum ether is added, the whole is left to itself for a few hours at 0°C and then filtered, to furnish 269 mg of crystalline $N^\epsilon$-tertiary butyloxycarbonyl-L-lysine methyl ester acetate, melting at 80°–81°C. The mother liquor further contains some $N^\epsilon$-tertiary butyloxycarbonyl-lysine methyl ester.

EXAMPLE 4

Eliminating the 2-p-tolyl-isopropyloxycarbonyl group 1. 432.6 Mg (1 mmol) of N-(2-p-tolyl-isopropyloxycarbonyl)-glycine dicyclohexyl ammonium salt are dissolved in 4.3 ml of a mixture of 7 parts by volume of glacial acetic acid, 1 part by volume of 82.8% formic acid and 2 parts by volume of water and stirred at room temperature. After 15 minutes and after 30 minutes a thin-layer chromatographic analysis each is carried out which reveals that after 15 minutes the splitting is about 95% and after 30 minutes quantitative. Likewise after 30 minutes, the solution is mixed with 20 ml of acetone, allowed to crystallize for a short time at 0°C, and the glycine is then filtered off and thoroughly washed with acetone. Yield: 69.5 mg = 92.7% of crystalline glycine.

2. When N-(2-p-tolyl-isopropyloxycarbonyl)-glycine ethyl ester is treated as described in Example 3 (2) for the corresponding 2-phenyl-isopropyloxycarbonyl compound with 80% acetic acid at 25°C, the protective group is split off quantitatively within 1½ hours.

EXAMPLE 5

Introducing the 2-p-diphenyl-isopropyloxycarbonyl group a. With the azide in aminoacid ester 106 Grams (0.5 mol) of p-diphenyldimethylcarbinol in 500 ml of methylenechloride and 60 ml of pyridine are mixed within 30 minutes at −5°C with a solution of 76 ml of chlorocarbonic acid phenyl ester in 250 ml of methylenechloride; the resulting suspension is stirred for 14 hours at 0°C, whereupon an almost clear solution is obtained which is evaporated to dryness under vacuum at 30°C in a rotary evaporator. The crystalline residue, consisting of 2-(p-diphenyl)-isopropyloxycarbonyl-phenyl ester, is dried for 1 hour under a high vacuum at room temperature, then mixed with 200 ml of dimethylformamide and 125 ml hydrazine-hydrate and while cooling with cold water the whole is stirred for 6 hours. The clear solution is slowly mixed with 1 liter of water while being cooled with ice, allowed to crystallize overnight at 0°C, and the crystals are then filtered off and washed with N-sodium hydroxide solution and water and dried under vacuum at 50°C. The resulting 2-(p-diphenyl)-isopropyloxycarbonyl hydrazide is recrystallized from 200 ml of carbon tetrachloride and 40 ml of petroleum ether. Yield: 103.0 g (= 76% of theory); melting point 108°–109°C.

While stirring a solution of 27 g (0.1 mol) of this hydrazide in 270 ml of acetonitrile at −25°C it is mixed with a solution of 50 ml of 6N-hydrochloric acid in 100 ml of acetonitrile and then with 22 ml of 5-molar sodium nitrite solution. After stirring the batch for 15 minutes at −15°C it is adjusted with 2N-soda solution to pH 6 to 7 and the solution is poured into much ice water. After stirring for a short time, the azide solidifies; it is filtered off and washed with ice water. The residue is dissolved in ether, the water separated, the ethereal solution dried over sodium sulfate and evaporated at room temperature under vacuum, to yield 28.3 g (= 100% of theory) of the azide in the form of a crystalline yellowish powder melting at 48°–52°C.

While stirring 3.37 g (20 mmols) of L-valine-methylester hydrochloride in 10 ml of dimethylformamide at 0°C there are added 2.8 ml of triethylamine, 6.2 g of the above azide and 5 ml of dimethylformamide. After 10 minutes another 2.8 ml of triethylamine are added and the whole is stirred on overnight at room temperature. The reaction mixture is diluted with 100 ml of ether, at 0°C repeatedly extracted with 0.1 molar citric acid solution and water, dried over sodium sulfate and evaporated to dryness under vacuum. The resulting ester is hydrolyzed as it is obtained. For this purpose the crude product is dissolved in 75 ml of isopropanol, mixed with 12 ml of 2N-sodium hydroxide solution, and the whole is stirred for 2½ hours at 40°C. Ether and water are then added to the solution, the aqueous solution is separated and mixed once more with water. The combined aqueous solutions are covered with ether, adjusted at 0°C with molar citric acid to pH = 2 and extracted with ether. The ethereal solution is washed neutral and dried, and then rendered alkaline with cyclohexylamine, whereupon the cyclohexyl ammonium salt crystallizes out. The ethereal solution is concentrated to about 50 ml, mixed with 50 ml of petroleum ether and allowed to crystallize at 0°C. The crystalline product is filtered off and washed with ether+λ petroleum ether (1 : 1), to yield 6.5 g of N-2-(p-diphenyl)-isopropyloxycarbonyl-L-valine cyclohexyl ammonium salt melting at 178°–180°C with decomposition.

b. With the azide in amino acids: 1.17 g (10 mmols) of L-valine are dissolved with heating in 9.1 g of a 10% aqueous solution of tetramethylammonium hydroxide. The solution is evaporated under vacuum at 80°C, and the residue is taken up three times in 5 ml of dimethylformamide and evaporated under vacuum. The crystalline residue is stirred with 20 ml of dimethylformamide at room temperature, mixed with 2.8 g of 2-p- diphenyloxycarbonyl azide, then with 3 ml of triethylamine and the suspension is stirred for 1 hour at room temperature, then mixed with ether and water, and the aqueous solution is separated, the ethereal solution extracted twice more with a little water and the combined aqueous solutions are acidified at 0°C to pH = 2. The aqueous solutions are extracted with ether, the ethereal extracts washed neutral, dried over sodium sulfate, filtered and rendered alkaline with cyclohexylamine. The cyclohexyl ammonium salt begins to crystallize immediately and is isolated as described under (a), to furnish 2.96 g of N-2-(p-diphenyl)-isopropyloxycarbonyl-L-valine-cyclohexyl ammonium salt melting at 178°–180°with decomposition.

c. With activated ester in aminoacids 1.17 Grams (10 mmols) of L-valine are dissolved in 4.55 ml of a 2.2N-methanolic solution of benzyltrimethylammonium hydroxide, evaporated to dryness under vacuum, once more dissolved in 10 ml of dimethylformamide and again evaporated under vacuum. The residue is taken up in 5 ml of dimethylformamide, mixed with 4.0 g of 2-(p-diphenyl)-isopropyloxycarbonyl phenyl ester and the whole is stirred for 4 hours at 50°C. The clear solution is mixed with 30 ml of water and 30 ml of ether and agitated; the aqueous phase is separated and adjusted at 0°C to pH = 2 with citric acid and extracted with ether. The ethereal extract is washed neutral, dried, filtered and mixed with 1.9 ml of cyclohexylamine, whereupon the cyclohexyl ammonium salt of N-2-(p-diphenyl)-isopropyloxycarbonyl-L-valine begins to crystallize immediately and is isolated as described under (a). The yield amounts to 3.15 g. Melting point 178°–180°C with decomposition.

In an identical manner the following N-2-(p-diphenyl)-isopropyloxycarbonyl derivatives can be prepared:

| Derivative | melting point |
|---|---|
| glycine-dicyclohexylammonium salt | 192–193°C (decomp.) |
| L-leucine | 227–230°C (decomp.) |
| L-proline-dicyclohexylammonium salt | 173–175°C (decomp.) |
| N $\epsilon$ -tertiary butyloxycarbonyl-L-lysine-dicyclohexylammonium salt | amorphous |
| L-tyrosine-cyclohexylammonium salt | 248–252°C (decomp.) sinters at 158°C |
| L-phenylalanine-dicyclohexylammonium salt | 116–119°C (decomp.) |
| L-glutamic acid-γ-tertiary butylester-cyclohexylammonium salt | 174–175°C (decomp.) |
| L-serine-tertiary butylether-cyclohexylammonium salt | 180–181°C (decomp.) |
| L-methionine-dicyclohexylammonium salt | 142–143°C |

2-(p-Diphenyl)-isopropyloxycarbonyl phenyl ester is prepared in the following manner:

21.2 Grams of p-diphenyl-dimethylcarbinol (0.1 mol) in 100 ml of methylenechloride and 12 ml of pyridine are mixed at −5°C within 30 minutes with a solution of 18.8 g of chlorocarbonic acid phenyl ester in 50 ml of methylenechloride. The batch is then stirred for 18 hours at 0°C, poured over ice water, the organic phase is isolated, repeatedly washed with water, dried and evaporated under vacuum at 30°C. The crystallizate obtained on recrystallization from ethyl acetate is washed with ethyl acetate+petroleum ether (2:1) and dried under vacuum at room temperature, to yield 25.8 g of 2-(p-diphenyl)-isopropyloxycarbonyl phenyl ester melting at 115°–116°C with decomposition.

EXAMPLE 6

Eliminating the N-2-(p-diphenyl)-isopropyloxycarbonyl group from different aminoacids 90.9 Mg (0.20 mmol) of N-2-(p-diphenyl)-isopropyloxycarbonyl-L-valine cyclohexylammonium salt are dissolved at 25°C in 2.0 ml of 80% acetic acid. After different intervals specimens of 0.2 ml each are taken, added to 4 ml of dimethylformamide and titrated with 0.1N-perchloric acid in glacial acetic acid. After 3½ hours the protective group has been quantitatively eliminated.

In an identical manner the splitting times of the following compounds in 80% acetic acid are determined:

| N-2-(p-diphenyl)-isopropyloxycarbonyl aminoacid | Quantitative elimination takes ... hours |
|---|---|
| Glycine-dicyclohexylammonium salt | 3 1/2 |
| L-leucine | 3 |
| L-proline-dicyclohexylammonium salt | 3 2/3 |
| N $\epsilon$ -tertiary butyloxycarbonyl-L-lysine-dicyclohexylammonium salt | 4 2/3 |
| L-tyrosine-cyclohexylammonium salt | 2 1/3 |
| L-phenylalanine-dicyclohexylammonium salt | 3 1/2 |
| L-glutamic acid-γ-tertiary butylester-cyclohexylammonium salt | 4 1/5 |
| L-serine-tertiary butylether-cyclohexylammonium salt | 3 |

EXAMPLE 7

Eliminating the N-2-(p-diphenyl)-isopropyloxycarbonyl group from N $\alpha$ -2-(p-diphenyl)-isopropyloxycarbonyl-N $\epsilon$ -BOC-L-lysyl-N $\epsilon$ -BOC-L-lysine methyl ester a. 160.0 mg of N $\alpha$ -2-(p-diphenyl)-isopropyloxycarbonyl-N $\epsilon$ -BOC-L-lysyl-N $\epsilon$ -BOC-L-lysine methyl ester are dissolved in 2.2 ml of a mixture of glacial acetic acid + 82.8% formic acid + water (7 : 1 : 2 parts by volume). After different intervals specimens of 0.3 ml each are taken, added to 4 ml of dimethylformamide and titrated with 0.1N-perchloric acid in glacial acetic acid. After 55 minutes the N $\alpha$ -protective group has been quantitatively eliminated, whereas the N $\epsilon$ -BOC groups have remained unaffected.

b. A solution of 240 mg of the above dipeptide derivative in 1.7 ml of methylenechloride is mixed at room temperature with 1.3 ml of a solution of 37.5 g of chloracetic acid in 12.5 ml of water. From the homogeneous solution specimens of 0.5 ml each are taken after different intervals, added to 1.5 ml of methanol and immediately chromatographed on silicagel in the system secondary butanol + glacial acetic acid + water (67 : 10 : 23). It is found that after 15 minutes the N $\alpha$ -protective group has been completely eliminated, whereas the N $\epsilon$ -BOC groups have remained unchanged.

The starting material may be prepared thus:

A mixture of 666 mg (1 mmol) of N $\alpha$ -2-(p-diphenyl)-isopropyloxycarbonyl-N $\epsilon$ -BOC-lysine dicyclohexylammonium salt and 4 ml of dimethylformamide is mixed at −15°C with 0.125 ml of pivaloylchloride. The whole is stirred for 15 minutes at −10°C and a solution of 320 mg (1 mmol) of N $\epsilon$ -BOC-lysine methyl ester acetate in 3 ml of dimethylformamide is added and the batch is stirred for 2 hours at 0°C, then taken up in ethyl acetate, at 0°C repeatedly washed with 0.1 molar citric acid solution, with 2N-soda solution and with water, dried and evaporated to dryness under vacuum. The residue is dissolved in a little ether, whereupon crystallization sets in rapidly, to yield 632 mg of N$^\alpha$ -2-(p-diphenyl)-isopropyloxycarbonyl-N$^\epsilon$ -BOC-lysyl-N$^\epsilon$ -BOC-lysine methyl ester melting at 87°–89°C with decomposition. After recrystallization from ethyl acetate + petroleum ether the melting point is still the same.

EXAMPLE 8

Eliminating the N-2-(p-diphenyl)-isopropyloxycarbonyl group from N-2-(p-diphenyl)-isopropyloxycarbonyl-L-prolyl-L-leucyl-L-(γ-tertiary butyl ester)-glutamyl-L-phenylalanine-tertiary butyl ester 1.10 G of N-2-(p-diphenyl)-isopropyloxycarbonyl-Pro-Leu-Glu(OtBu)-Phe-OtBu are stirred for 2¼ hours with 6.5 ml of a mixture of glacial acetic acid + 82.8% formic acid + water (7 : 1 : 2 by volume). While cooling with ice, the batch is rendered alkaline with saturated potash solution, extracted with ethyl acetate, washed neutral, dried and evaporated to dryness under vacuum. The residue is triturated with a small quantity of petroleum ether and recrystallized from 75% methanol, to yield 0.65 g of H-Pro-Leu-Glu(OtBu)-Phe-OtBu melting at 188°–190°C.

The starting material is accessible in the following manner:

5.35 Grams (10 mmols) of N-2-(p-diphenyl)-isopropyloxycarbonyl-proline dicyclohexylammonium salt in 40 ml of dimethylformamide are mixed at −15°C with 1.25 ml of pivaloylchloride, stirred for 15 minutes at −10°C and a solution of 5.8 g of H-Leu-Glu(OtBu)-Phe-OtBu acetate in 30 ml of dimethylformamide is dropped in. The mixture is allowed to react for 2 hours at 0°C, then diluted with ethyl acetate and the solution is agitated at 0°C twice each with water, 0.1 molar citric acid solution, 2N-soda solution and water. The ethyl acetate solution is dried over sodium sulfate and evaporated to dryness; the residue is dissolved in ether and caused to crystallize, to yield 6.75 g of N-2-(p-diphenyl)-isopropyloxycarbonyl-Pro-Leu-Glu(OtBu)-Phe-OtBu which, after recrystallization from 85% methanol, melts at 188°C with decomposition.

EXAMPLE 9

Using the N-2-(p-diphenyl)-isopropyloxycarbonyl group in the solid phase synthesis Manufacturing carbobenzoxy-L-phenylalanyl-L-(N$^\epsilon$ -tertiary butyloxycarbonyl)-lysyl-glycine hydrazide:

2.15 Grams of BOC-glycine resin [styrene + divinylbenzene copolymer containing 0.25 milliequivalent of BOC-glycine/gram resin = 0.5 mmol] are stirred for 3 minutes with 10 ml of dioxane, then filtered. Then 10 ml of 4N-hydrochloric acid in dioxane are added and the whole is stirred for 30 minutes at room temperature and washed with 3 × 10 ml of dioxane and methylenechloride, stirring in each case with the solvent for 3 minutes. The batch is then mixed with 10 ml of a mixture of methylenechloride + triethylamine (9 : 1) and stirred for 10 minutes and rinsed with 6 × 10 ml of methylenechloride. The H-glycine resin is stored under methylenechloride.

0.83 Gram of N$^\alpha$ -2-(p-diphenyl)-isopropyloxycarbonyl-N$^\epsilon$ -BOC-lysine dicyclohexylammonium salt (1.25 mmols) are dissolved in methylenechloride and agitated at 0°C 3 times each with 0.2 molar citric acid and water. The methylene chloride solution is dried, filtered and concentrated to a few ml under vacuum. This solution is added to the above resin, stirred for 5 minutes, then a solution of 290 mg of dicyclohexylcarbodiimide in a little methylenechloride is added. The batch is stirred for 3 hours, filtered and washed with 3 × 10 ml each of methylenechloride, dimethylformamide, dimethylformamide + methanol (1 : 1) and methylenechloride. The N -2-(p-diphenyl)-isopropyloxycarbonyl-N -BOC-Lys-Gly resin is then suspended in 5 ml of methylenechloride and 3.7 ml of a solution of 37.5 g of chloracetic acid in 12.5 ml of water is added, the whole stirred on for 1½ hours and then washed as described above with methylenechloride, dioxane, methylenechloride, methylenechloride + triethylamine (9 : 1) and methylenechloride. The resulting H-Lys(-BOC)-Gly resin is mixed with 0.37 g of carbobenzoxy-L-phenylalanine (Z-Phe-OH) in 8 ml of methylenechloride and stirred for 5 minutes, then 290 mg of dicyclohexylcarbodiimide in a little methylenechloride is added and the whole is stirred for 3 hours. The Z-Phe-Lys(BOC)-Gly resin is again filtered as described above and washed with methylenechloride, dimethylformamide, dimethylformamide + methanol (1 : 1), methanol and ethanol, then stirred for 15 hours with 10 ml of ethanol + hydrazine hydrate (3 : 1), filtered off and repeatedly washed with ethanol. The combined filtrates are evaporated to dryness under vacuum, and the residue is freed from hydrazine hydrate by being dried in a high vacuum over concentrated sulfuric acid at 50°C. The residue is dissolved in 5 ml of boiling ethanol, a small quantity of undissolved matter is filtered off and the filtrate is mixed hot with about 15 ml of water. The batch is seeded, then allowed to cool slowly to room temperature, and the product which crystallizes out is filtered off and washed with ethanol + water (1 : 3), to furnish 185 mg of Z-Phe-Lys(BOC)-Gly-NHNH$_2$ melting at 163°–164°C.

EXAMPLE 10

Preparation of L-prolyl-L-tyrosyl-(N$^\epsilon$ -tertiary butyloxycarbonyl)-L-lysyl-L-methionine hydrazide with the use of the 2-para-diphenylisopropyloxycarbonyl group a. 6.7 g (10 mmols) of N$^\alpha$ -2-(para-diphenyl)-isopropyloxycarbonyl-N$^\epsilon$ -BOC-L-lysine-dicyclohexylammonium salt in 40 ml of dimethylformamide are stirred at −15°C while being treated with 1.25 ml of pivaloyl chloride, then stirred at −10°C for 5 minutes. Under a current of nitrogen, 2.0 g of L-methionine-methylester hydrochloride and 1.4 ml of triethylamine are then added, and the batch stirred at 0°C for 3 hours. It is then diluted with ethyl acetate, washed at 0°C 3 times with 0.1-molar citric acid solution, and at room temperature three times with 2N-potassium carbonate solution and three times with water, then dried and evaporated to dryness under reduced pressure. The crude product (6.5 g) is filtered through a column of 150 g of silica gel, and 4.7 g of N$^\alpha$ -2-(para-diphenyl)-isopropyloxycarbonyl-N$^\epsilon$ -BOC-L-lysyl-L-methionine-methyl ester obtained in the form of a colorless resin. Rf = 0.55 in chloroform + acetone (8:2).

b. 3.15 G (5 mmols) of this dipeptide ester are stirred for an hour and a half with 50 ml of a mixture of glacial acetic acid, 82.8% formic acid and water (7 : 1 : 2 by volume), then poured into a mixture of 50 ml of ethyl acetate and 20 ml of saturated potassium carbonate solution at 0°C. The ethyl acetate solution is washed with water, dried and carefully evaporated. The resulting $N^\epsilon$-BOC-L-lysyl-L-methioninemethyl ester is unstable and must be processed immediately.

c. To this end, the residue is dissolved at 0°C in 18 ml of acetonitrile under nitrogen, treated with a solution of 2.10 g (5 mmols) of N-2-(para-diphenyl)-isopropyloxycarbonyl-L-tyrosin (liberated from the cyclohexylammonium salt by means of citric acid) in 2 ml of dimethylformamide and 1.15 g of dicyclohexyl-carbodiimide, and stirred at 0°C for 20 hours. The dicyclohexylurea which precipitates is filtered off, the filtrate evaporated, the residue triturated with ether + petroleum ether, filtered off, and reprecipitated from ethyl acetate + petroleum ether. There are obtained 2.8 g of N-2-(para-diphenyl)-isopropyloxycarbonyl-L-tyrosyl-$N^\epsilon$-BOC-L-lysyl-L-methionine-methylester in the form of a powder which is unitary according to thin layer chromatography; Rf = 0.2 in chloroform + acetone (8:2).

d. 2.38 g (3 mmols) of this tripeptide ester are stirred with 30 ml of a mixture of glacial acetic acid + 82.8% formic acid + water (7 : 1 : 2 by volume) for 1 hour at room temperature. The solution is poured into ice water, extracted twice with ether, the aqueous solution rendered alkaline with saturated potassium carbonate solution, and extracted with ethyl acetate. On evaporation of the ethyl acetate there remain 1.33 g of L-tyrosyl-$N^\epsilon$-BOC-L-lysyl-L-methioninemethyl ester in the form of a colorless foam. Rf = 0.5 in chloroform + methanol (85:15).

e. 1.11 G (2 mmols) of this tripeptide ester and 0.71 g (2 mmols) of N-2-(para-diphenyl)-isopropyloxycarbonyl-L-proline (liberated from the dicyclohexylammonium salt) are dissolved in 6 ml of acetonitrile, the solution treated at 0°C with 450 mg of dicyclohexylcarbodiimide, and stirred at 0°C for 18 hours. The dicyclohexylurea which precipitates is filtered off, the filtrate diluted with ethyl acetate, extracted by agitation at 0°C three times with 0.1-molar citric acid, at room temperature with 2N-potassium carbonate solution and water, then dried, and evaporated to dryness under reduced pressure. N-2-(para-diphenyl)-isopropyloxycarbonyl-L-prolyl-L-tyrosyl-$N^\epsilon$-BOC-L-lysyl-L-methionine-methyl ester is obtained in quantitative yield (1.8 g).

f. The methyl ester is stirred for 1 hour with 22 ml of a 7 : 1 : 2-mixture of glacial acetic acid, 82.8% formic acid and water. The solution is treated with iced water, extracted twice with ether, the aqueous solution is given an alkaline reaction with saturated potassium carbonate solution, and extracted with ethyl acetate. After drying, the ethyl acetate is completely expelled under reduced pressure. There remain behind 1.02 g of L-prolyl-L-tyrosyl-$N^\epsilon$-BOC-L-lysyl-L-methionine-methyl ester; Rf = 0.25 in chloroform + methanol (85:15). The product can be crystallized from acetonitrile. Melting point, 177°–180°C.

g. 326 Mg (0.5 mmol) of the tetrapeptide ester are dissolved in 1 ml of hot methanol, treated at room temperature with 0.25 ml of hydrazine hydrate while nitrogen passes over, then kept under seal for 18 hours. The product which crystallizes is filtered off and washed with water. 225 Mg of L-prolyl-L-tyrosyl-$N^\epsilon$-BOC-L-lysyl-L-methionine hydrazide of melting point 206°–207°C are obtained.

EXAMPLE 11

Preparation of L-prolyl-L-tyrosyl-$N^\epsilon$-tertiary butyloxycarbonyl-L-lysyl-L-methionine hydrazide by the solid phase synthesis with the use of the 2-(para-diphenyl)-isopropyloxycarbonyl group a. In a nitrogen atmosphere in a reaction vessel of 50 ml capacity according to Merrifield, 4.9 g of BOC-methionine resin (styrol-divinylbenzene-copolymer containing 0.18 m equivalent BOC-methionine/g resin = 0.88 mmol) are agitated in turn with the following reagents which are each filtered off before the next is used:

1. 25 ml of dioxan for 4 minutes;
2. 20 ml of 4N-HCl in dioxan for 60 minutes;
3. 3 × 20 ml of dioxan for 3 minutes each time;
4. 3 × 20 ml of ethanol for 3 minutes each time;
5. 3 × 20 ml of chloroform for 3 minutes each time;
6. 20 ml of chloroform + triethylamine (9:1) for 10 minutes;
7. 3 × 20 ml of chloroform for 3 minutes each time;
8. 4 × 20 ml of methylene chloride for 3 minutes each time.

The resulting methionine resin is stored moist with methylene chloride (it contains a total of 17 ml of methylene chloride). From 1.87 g of $N^\alpha$-2-(para-diphenyl)-isopropyloxycarbonyl-$N^\epsilon$-tertiary butyloxycarbonyl-L-lysine-dicyclohexylammonium salt the protected L-lysine is liberated as described in Example 9. The resulting methylene chloride solution is added to the aforementioned resin, the whole agitated for 10 minutes, then a solution of 730 mg of dicyclohexylcarbodiimide in 3 ml of methylene chloride is added, and the whole agitated for 4 hours. The resin is then washed while being agitated with 3 × 20 ml of methylene chloride (3 minutes each time);
3 × 20 ml of methanol (3 minutes each time); and
3 × 20 ml of methylene chloride (3 minutes each time).

The resulting $N^\alpha$-2-(para-diphenyl)-isopropyloxycarbonyl-$N^\epsilon$-BOC-L-lysyl-L-methionine resin (which contains 17 ml of methylene chloride) is treated with 12.6 ml of a 75% aqueous chloracetic acid solution and agitated for an hour and a half to eliminate the $N^\alpha$-2-(para-diphenyl)-isopropyloxycarbonyl group. The resin is filtered off and washed while being agitated with:

3 × 20 ml of methylene chloride (3 minutes each time);
4 × 20 ml of ethanol (3 minutes each time);
25 ml of chloroform (3 minutes);
20 ml of chloroform + triethylamine (9:1) (10 minutes);
3 × 20 ml of chloroform (3 minutes each time);
3 × 20 ml of methanol (3 minutes each time); and
3 × 20 ml of methylene chloride (3 minutes each time).

In a manner analogous to that described above, the resulting $N^\epsilon$-BOC-L-lysyl-L-methionine resin is reacted with N-2-(para-diphenyl)-isopropyloxycarbonyl-L-tyrosine. To this end, 1.6 g of the cyclohexylammonium salt of this compound are stirred at 0°C with 25 ml of ethyl acetate and 20 ml of a 1-molar citric acid solution until dissolution is complete. The aqueous layer is separated, the ethyl acetate solution is washed, dried, and evaporated to dryness in vacuo. The crystalline residue is dissolved in 1 ml of dimethyl formamide, diluted with 10 ml of methylene chloride, and the solution added to the aforementioned resin. At the same time, 710 mg of hydroxysuccinimide are added. The batch is agitated for 10 minutes, and a solution of 700 mg of dicyclohexylcarbodiimide in 5 ml of methylene chloride then added, and the whole is agitate for 4 hours. The resin is then washed as described above with methylene chloride, methanol and methylene chloride. For the elimination of the N-2-(para-diphenyl)-isopropyloxycarbonyl group with chloroacetic acid the above procedure is followed exactly. L-Tyrosyl-N $^\epsilon$ -BOC-L-lysyl-L-methionine resin is obtained which is condensed with N-2-(para-diphenyl)-isopropyloxycarbonyl-L-proline in methylene chloride (obtained from a solution of 1.34 g of the dicyclohexylammonium salt in methylenechloride by liberation with citric acid). The resulting methylene chloride solution is agitated with the resin for 10 minutes, a solution of 580 mg of dicyclohexylcarbodiimide in 5 ml of methylene chloride is added, and the whole agitated for 18 hours. The resin is filtered off, washed as afore-described, and the N-2-(para-diphenyl)-isopropyloxycarbonyl group split off with chloracetic acid. After the usual washing procedures, the resulting L-propyl-L-tyrosyl-N $^\epsilon$ -BOC-L-lysyl-L-methionine resin is agitated with 20 ml of ethanol, filtered and, under a weak current of nitrogen, stirred with 7 ml of ethanol and 3 ml of hydrazine hydrate for 17 hours. The resin is filtered off and washed ten times with 10 ml of 95% ethanol each time. The combined filtrates are evaporated under reduced pressure at 50°C and the residue dried in a high vacuum over sulfuric acid. The crude product is dissolved in 25 ml of 0.1N-acetic acid and 80 ml of ethyl acetate, and the aqueous solution agitated with 2 × 50 ml of ethyl acetate. The three ethyl acetate solutions are extracted twice with 10 ml each time of 0.1-normal acetic acid. The three aqueous extracts are combined and lyophilized. Further purification is performed by chromatography over 7 g of CM-Sephadex (Registered Trade Mark) by means of a gradient consisting of 300 ml of 0.01-molar ammonium acetate and 300 ml of 0.05 molar ammonium acetate pH 6.5. The pure fractions are combined and lyophilized. 320 Mg of the acetate of L-prolyl-L-tyrosyl-N $^\epsilon$ -BOC-L-lysyl-L-methionine hydrazide are obtained. The product is fully identical with the product described in Example 10. Rf = 0.35 in the thin-layer chromatogram, system s-butanol + glacial acetic acid + water (67:10:23). The basic product is liberated from the acetate by means of potassium carbonate solution and then crystallizes from aqueous methanol. Melting point 206°–207°C (with decomposition).

EXAMPLE 12

Preparation of N-2-(para-diphenyl)-isopropyloxycarbonyl-L-leucyl-L-valyl-S-trityl-L-cysteinyl-glycyl-L-glutamic acid-di-tertiary butyl ester.

The starting material, S-trityl-L-cysteinyl-glycyl-L-glutamic acid-di-tertiary butylester, can be prepared as follows: From carbobenzoxy-glycine and L-glutamic acid-di-tertiary butyl ester, carbobenzoxyglycyl-L-glutamic acid-di-tertiary butylester is obtained by the mixed anhydride method. Melting point, 74°–76°C. The glycyl-L-glutamic acid-di-tertiary butylester obtained therefrom by hydrogenation is reacted with N,S-di-trityl-L-cystein and dicyclohexylcarbodiimide and yields N,S-Di-trityl-L-cysteinyl-glycyl-L-glutamic acid-di-tertiary butylester melting at 98°–110°C. On elimination of the N-trityl group with 80% acetic acid, S-trityl-L-cysteinyl-glycyl-L-glutamic acid-di-tertiary butyl ester is obtained.

N-2-(para-diphenyl)-isopropyloxycarbonyl-L-valin (liberated from 1.91 g (4.2 mmols) of the cyclohexylammonium salt by means of citric acid) is dissolved in 20 ml of ethyl acetate, and the solution treated with 0.59 ml (4.2 mmols) of triethylamine and, after cooling to −10°C, with 0.56 ml (4.2 mmols) of chlorocarbonic acid-isobutyl ester. The batch is stirred for 10 minutes at −10°C before a solution of 2.78 g (4.2 mmols) of the above tripeptide-diester in 25 ml of ethyl acetate is added dropwise, and then stirred on for 15 minutes at −10°C and 1 hour at room temperature. After dilution with ethyl acetate, the batch is extracted by agitation with 0.5-molar citric acid, N-sodium bicarbonate, and water at 0°C, dried, and evaporated to dryness. The residue is crystallized from acetone + ether to obtain 2.91 g of N-2-(para-diphenyl)-isopropyloxycarbonyl-L-valyl-S-trityl-L-cysteinyl-glycyl-L-glutamic acid-di-tertiary butyl ester melting at 184°–186°C. Rf = 0.6 in chloroform + methanol (95:5).

1 G (1 mmol) of this tetrapeptide ester is stirred at room temperature for 1 hour with 10 ml of a mixture of glacial acetic acid, 82.8% formic acid, and water (7:1:2 by volume). After the addition of 10 ml of water and 40 ml of chloroform, the batch is given an alkaline reaction with concentrated ammonia at 0°C, the chloroformic solution separated, washed, dried and evaporated to dryness. The residue is triturated with petroleum ether to obtain 0.76 g of L-valyl-S-trityl-L-cysteinyl-glycyl-L-glutamic acid-di-tertiary butyl ester in the form of an oil which is unitary according to thin-layer chromatography. Rf = 0.25 in chloroform + methanol (95:5). At 0°C, 238 mg of dicyclohexylcarbodiimide are added to 370 mg (1 mmol) of N-2-(para-diphenyl)-isopropyloxy carbonyl-L-leucine and 768 mg of the above tetrapeptide ester in 7 ml of tetrahydrofuran, and the whole is stirred at 0°C for 4 hours. Filtering off the dicyclohexylurea is followed by dilution with ethyl acetate, washing at 0°C with 0.5 molar citric acid, N-sodiumbicarbonate and water, drying, and evaporation. By elution with ethyl acetate in the chromatography on silica gel, 775 mg of N-2-(para-diphenyl)-isopropyloxycarbonyl-L-leucyl-L-valyl-S-trityl-L-cysteinyl-glycyl-L-glutamic acid-di-tertiary butylester are obtained as a unitary product. Rf = 0.55 in chloroform + methanol (9:1); Rf = 0.63 in tolueneacetone (1:1).

EXAMPLE 13

Introduction of the 1,1-diphenyl-ethoxycarbonyl group 8.2 G of diphenyl-methyl-carbinol, 5.35 g of isocyanate-acetic acid ethyl ester and 4 ml of pyridine are heated at 50°C for 48 hours. The solution is diluted with 100 ml of ether, extracted at 0°C with 0.1-molar citric acid solution and water, dried over sodium sulfate, and evaporated completely under reduced pressure. There are obtained 10.6 g of viscous oil consisting of 1,1-diphenyl-ethoxycarbonyl-glycine-ethyl ester. Rf = 0.7 in the thin-layer chromatography in chloroform + methanol (95:5).

EXAMPLE 14

Splitting off the 1,1-diphenyl-ethoxy-carbonyl group 207.8 Mg of 1,1-diphenylethoxycarbonyl-glycine-ethyl ester are dissolved at 25°C in 3.15 ml of 80% acetic acid. At different times, test portions of 0.20 ml are taken, added to 4 ml of dimethylformamide, and the liberated glycine ethyl ester titrated with 0.1N-perchloric acid. The half-life period for the elimination of the protective group is about 30 minutes. After 5 hours the elimination is quantitative.

EXAMPLE 15

Introduction of the 1,1-diphenyl-propyloxycarbonyl group 3.2 G of diphenyl-ethyl-carbinol, 1.9 g of isocyanate acetic acid ethyl ester and 1.6 ml of pyridine are heated at 50°C for 72 hours. The solution is diluted with 50 ml of ether, washed several times at 0°C with 0.1-molar citric acid solution and water, dried over sodium sulfate, and completely evaporated under reduced pressure. After elimination of 2.3 g of diphenylethylcarbinol by means of petroleum ether, 1,1-diphenyl-propyloxycarbonyl-glycine-ethyl ester is obtained in the form of an oil; Rf = 0.2 in the thin-layer chromatogram in chloroform.

EXAMPLE 16

Elimination of the 1,1-diphenyl-propyloxycarbonyl group

409 Mg of 1,1-diphenyl-propyloxycarbonyl-glycine-ethyl ester are dissolved at 22°C in 80% acetic acid. At different times test portions of 0.5 ml are taken, added to 4 ml of dimethylformamide, and the liberated glycine ethylester titrated with 0.1N-perchloric acid. The half-life period for the elimination of the protective group is about 50 minutes. After 8 hours the protective group is split off quantitatively.

We claim:

1. A compound of the formula II

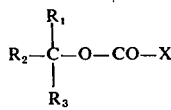

in which $R_1$ is lower alkyl, $R_2$ is lower alkyl or phenyl and $R_3$ is phenyl and wherein phenyl is unsubstituted or substituted by lower alkyl, phenyl or lower alkylphenyl and X stands for phenyloxy or p-nitrophenyloxy.

2. A compound of claim 1, wherein $R_1$ and $R_2$ each represents a methyl or ethyl group, $R_3$ has the same meaning as in claim 1, and X is phenyloxy.

3. A compound of claim 1, wherein $R_3$ represents a phenyl, tolyl or biphenylyl group, and $R_2$ stands for lower alkyl, and X is phenyloxy.

4. A compound of claim 1, wherein $R_1$ stands for methyl or ethyl, $R_2$ and $R_3$ each stands for phenyl, and X is phenyloxy.

5. A compound of claim 1, wherein the

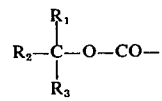

group is the 2-phenyl-isopropyloxycarbonyl group or the 1,1-diphenylethyloxycarbonyl group.

6. A compound of claim 1, wherein the

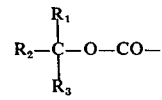

group is the 2-para-tolylisopropyloxycarbonyl group, and X is phenyloxy.

7. A compound of claim 1, wherein the

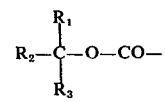

group is the 2-(para-biphenylyl)-isopropyloxycarbonyl group, and X is phenyloxy.

* * * * *